United States Patent
Calias et al.

(10) Patent No.: US 6,749,865 B2
(45) Date of Patent: Jun. 15, 2004

(54) MODIFICATION OF BIOPOLYMERS FOR IMPROVED DRUG DELIVERY

(75) Inventors: Pericles Calias, Melrose, MA (US); Robert J. Miller, Halifax, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/784,402

(22) Filed: Feb. 15, 2001

(65) Prior Publication Data

US 2003/0087877 A1 May 8, 2003

Related U.S. Application Data

(60) Provisional application No. 60/182,558, filed on Feb. 15, 2000, and provisional application No. 60/211,508, filed on Jun. 14, 2000.

(51) Int. Cl.$^7$ .......................... A61K 9/00; A61K 38/46; A61K 38/00; C12N 11/02; C07K 17/02
(52) U.S. Cl. .................. 424/484; 424/94.6; 424/94.61; 424/485; 424/486; 424/487; 424/488; 435/177; 435/178; 435/180; 435/181; 436/528; 436/532; 514/2; 530/408; 530/812; 530/816
(58) Field of Search .............................. 424/94.61, 484; 435/174, 177, 180, 181, 178; 426/94.6, 485, 486, 487, 488; 436/528, 532; 514/2; 530/408, 812, 816

(56) References Cited

U.S. PATENT DOCUMENTS

| | | | |
|---|---|---|---|
| 4,582,865 A | 4/1986 | Balazs et al. | 524/29 |
| 4,636,524 A | 1/1987 | Balazs et al. | 514/781 |
| 4,937,270 A | 6/1990 | Hamilton et al. | 514/777 |
| 5,017,229 A | 5/1991 | Burns et al. | 106/162 |
| 5,157,123 A * | 10/1992 | Zara et al. | 546/291 |
| 5,169,934 A | 12/1992 | Clark et al. | 530/327 |
| 5,354,853 A | 10/1994 | Staveski et al. | 536/17.1 |
| 5,362,478 A | 11/1994 | Desai et al. | 424/9 |
| 5,439,686 A | 8/1995 | Desai et al. | 424/451 |
| 5,451,661 A | 9/1995 | Wan | 530/345 |
| 5,496,872 A | 3/1996 | Constancis et al. | 523/118 |
| 5,498,421 A | 3/1996 | Grinstaff et al. | 424/450 |
| 5,527,893 A | 6/1996 | Burns et al. | 514/53 |
| 5,560,933 A | 10/1996 | Soon-Shiong et al. | 424/489 |
| 5,585,361 A | 12/1996 | Burns et al. | 514/25 |
| 5,635,207 A | 6/1997 | Grinstaff et al. | 424/450 |
| 5,639,473 A | 6/1997 | Grinstaff et al. | 424/450 |
| 5,760,200 A | 6/1998 | Miller et al. | 536/21 |
| 5,760,220 A | 6/1998 | Giguere et al. | 540/521 |
| 5,855,987 A * | 1/1999 | Margel et al. | 428/195 |
| 5,874,417 A * | 2/1999 | Prestwich et al. | 514/54 |
| 5,902,795 A | 5/1999 | Toole et al. | 514/54 |
| 5,932,552 A | 8/1999 | Blanchard et al. | 514/21 |
| 6,030,958 A | 2/2000 | Burns et al. | 514/57 |
| 6,174,999 B1 | 1/2001 | Miller et al. | 536/21 |
| 6,235,726 B1 | 5/2001 | Burns et al. | 514/57 |

FOREIGN PATENT DOCUMENTS

| | | |
|---|---|---|
| WO | WO 91/14696 | 10/1991 |
| WO | WO 93/08842 | 5/1993 |
| WO | WO 98/52614 | 11/1998 |
| WO | WO 99/26595 | 6/1999 |
| WO | WO 99/66063 | 12/1999 |

OTHER PUBLICATIONS

Pouyani et al., "Functionalized Derivatives of Hyaluronic Acid Oligosaccharides: Drug Carriers and Novel Biomaterials", *Advance ACS Abstracts*, pp. 339–347, May 1, 1994.

Mason et al., "Attachment of hyaluronic acid to polypropylene, polystyrene, and polytetrafluoroethylene", *Biomaterials*, vol. 21, No. 1., pp. 31–36, (2000).

Danishefsky et al., Conversion of Carboxyl Groups of Mucopolysaccharides into Amides of Amino Acid Esters, *Carbohydrate Reseaech*, vol. 16, pp. 199–205 (1971).

Sparer et al., Controlled Release from Glycosaminoglycan Drug Complexes, Controlled Release Delivery Systems, Chapter 6, pp. 107–119 (1983).

Raja et al., Preparation of Alkylamine and $^{125}$I–Radiolabeled Derivatives of Hyaluronic Acid Uniquely Modified at the Reducing End, Analytical Biochemistry, vol. 139, pp. 168–177 (1984).

Wu, et al., Receptor–mediated in Vitro, Gene Transformation by a Soluble DNA Carrier System, the *Journal of Biological Chemistry*, vol. 262, No. 10, pp. 4429–4432 (1987).

Dadley–Moore, D. L., Synthetic peptide antigens induce antibodies to *Taenia ovis* oncospheres, *Vaccine*, vol. 17, pp. 1506–1515 (1999).

Bernkop–Schnurch et al., Development of controlled drug release systems based on thiolated polymers, J. Controlled Release, vol., 66, pp. 39–48 (2000).

* cited by examiner

*Primary Examiner*—David M. Naff
(74) *Attorney, Agent, or Firm*—Isabelle A. S. Blundell (57) ABSTRACT

A biologically active conjugate is disclosed comprising a biopolymer and a therapeutic agent joined by a disulfide bond. The conjugate, when formulated in a pharmaceutical composition with a suitable carrier, has improved in vivo stability and activity, and can be targeted to a variety of cells, tissues and organs.

16 Claims, 3 Drawing Sheets

MODIFICATION OF BIOPOLYMERS FOR IMPROVED DRUG DELIVERY

This application claims priority to U.S. Provisional Application No. 60/182,558 filed Feb. 15, 2000 and to U.S. Provisional Application No. 60/211,508 filed Jun. 14, 2000. This invention relates to the chemical modification of biopolymers for the delivery of therapeutic agents, such as therapeutic proteins, to specific tissues, organs or cells within a subject, or to extend the bioavailability of the therapeutic agent by enhancing its in vivo stability. The biopolymer is initially modified to introduce one or more disulfide bonds into a side chain of the biopolymer. This facilitates the reaction of the biopolymer with a therapeutic agent that has also been modified to present a reactive thiol moiety to form the biopolymer-therapeutic agent conjugate. The site-specific reaction of the biopolymer and the therapeutic agent increases the stability of the therapeutic agent upon delivery to the desired site targeted by the biopolymer.

BACKGROUND OF THE INVENTION

Biopolymers are biocompatible polymers that are useful for a wide variety of biomedical applications, such as for surgical aids, to prevent or reduce the formation of surgical adhesions, and for drug delivery applications. Many biopolymers are naturally occurring substances found in the body, and therefore do not have any unacceptable toxic or injurious effects on biological function. An example of such a biopolymer is hyaluronic acid ("HA"), a naturally occurring mucopolysaccharide found, for example, in synovial fluid, in vitreous humor, in blood vessel walls and the umbilical cord, and in other connective tissues. Hyaluronic acid consists of alternating N-acetyl-D-glucosamine and D-glucuronic acid residues joined by alternating $\beta$ 1-3 glucuronidic and $\beta$ 1-4 glucosaminidic bonds, so that the repeating unit is—$(1\rightarrow4)$-$\beta$-D-GlcA-$(1\rightarrow3)$-$\beta$-D-GlcNAc—. In water, hyaluronic acid dissolves to form a highly viscous fluid. The molecular weight of hyaluronic acid isolated from natural sources generally falls within the range of $5\times10^4$ up to $1\times10^7$ daltons.

U.S. Pat. No. 4,582,865, to Balazs et al. states, inter alia, that cross-linked gels of HA can slow the release of a low molecular weight substance that is dispersed therein but not covalently attached to the gel macromolecular matrix. See, also, U.S. Pat. No. 4,636,524, which contains a disclosure of related technology. Both of these patents describe HA compositions in which the HA is crosslinked by reaction with divinyl sulfone, and the use of the crosslinked HA compositions in drug delivery applications.

R. V. Sparer et al., 1983, Chapter 6, pages 107–119, in T. J. Roseman et al., Controlled Release Delivery Systems, Marcel Dekker, Inc., New York, describes sustained release of chloramphenicol covalently attached to hyaluronic acid by an ester linkage, either directly or in an ester complex including an alanine bridge as an intermediate linking group. The HA is modified by attaching cysteine residues to the HA via amide bonds, and then the cysteine-modified HA is crosslinked by forming disulfide bonds between the attached cysteine residues. Similarly, I. Danishefsky et al., 1971, in Carbohydrate Res., Vol. 16, pages 199–205, describe the modification of a mucopolysaccharide by converting the carboxyl groups of the mucopolysaccharide into substituted amides by reacting the mucopolysaccharide with an amino acid ester in the presence of 1-ethyl-3-(3-dimethylaminopropyl) carbodiimide hydrochloride ("EDC") in aqueous solution. See, also, U.S. Pat. No. 4,937,270 and U.S. Pat. No. 5,760,220 which describe the modification of hyaluronic acid by reaction of the carboxyl groups of the biopolymer with a nucleophile to produce a water insoluble amide, and the use of those compositions for controlled release drug delivery.

A series of patents assigned to VivoRx Pharmaceuticals, Inc., describe compositions for the in vivo delivery of insoluble pharmaceutically active agents. Delivery of the drug substances is achieved, for instance, by encasing the active agent in a polymeric shell formed from a biocompatible polymer. The biocompatible polymer may be protein, lipid, DNA molecule or polysacharide, and the pharmaceutically active agent may be a therapeutic protein such as taxol. The polymer contains covalently attached sulfhydryl groups or disulfide linkages which can be crosslinked to form disulfide bonds. The polymeric shell is formed using ultrasonic irradiation techniques. These compositions are described as being less toxic, being more soluble, and having improved targeting as compared to prior art compositions. Relevant VivoRx patents include U.S. Pat. Nos. 5,498,421; 5,439,686; U.S. Pat. No. 5,362,478; U.S. Pat. No. 5,635,207; U.S. Pat. No. 5,560,933; U.S. Pat. No. 5,635,207 and U.S. Pat. No. 5,639,473.

U.S. Pat. No. 5,496,872 relates to biocompatible and biodegradable crosslinkable polymers having reactive thiol groups. The reactive thiol groups can be crosslinked to form disulfide linkages between adjacent molecules, resulting in a three dimensional network. These polymers can be used for binding tissues or binding tissues with implanted biomaterials.

U.S. Pat. No. 5,932,552 describes a keratin hydrogel having biomedical applications. The hydrogel is formed from crosslinked keratin bound by disulfide linkages. Among the biomedical applications described in the patent are uses of the hydrogels for cell scaffolding in tissue repair.

U.S. Pat. Nos. 5,354,853 and 5,451,661 describe, respectively, the preparation of phospholipid-saccharide conjugates, and lipids conjugated to biologically active agents such as peptides, proteins and nucleic acids. These conjugates are described as being particularly useful in drug delivery applications.

U.S. Pat. No. 5,902,795, to Toole et al., discloses hyaluronic acid oligosaccharides, having between one and sixteen repeating units, which are used to treat tumors in mammals. The patent states that the oligosaccharides act to reduce the level of membrane-associated hyaluronan-binding proteins, which are expressed on the surface of certain tumor cells during cell migration. The treatment is believed to reduce the incidence of tumor metastasis in the mammals.

A. Burnkop-Schnurch et al., J. Controlled Release, 2000, 66, 39, describes the synthesis of carboxymethyl cellulose ("CMC") and polycarbophil modified with L-cysteine using carbodiimide chemistry. The polymers are reacted with the cysteine to form an amide bond between the primary amino group of the amino acid and the carboxylic acid of the polymer. The thiolated polymers were allowed to oxidize to form disulfide bridges. The dissolution of these tablets, both with and without drugs, was analyzed. The tablets were found to have improved stability and viscoelasticity.

Copending U.S. patent application Ser. No. 09/430,857 now abandoned relates to surfaces that have been modified by the attachment of hyaluronic acid. The surface can be part of a medical device, such as a stent or a surgical tubing. The surface is modified to include a reactive amino group that reacts with a derivatized hyaluronic acid. The modified devices and instruments are hydrophilic, and have antifouling and anti-platelet adhesion characteristics, thereby producing a reduction in risks associated with thrombosis.

The conjugated biopolymers of this invention represent a significant improvement over drug delivery vehicles of the prior art due, in part, to the site-specific reaction between the biopolymer and the therapeutic agent which increases the stability and activity of the therapeutic agent upon delivery to the desired site within a subject.

SUMMARY OF THE INVENTION

The present invention features a biopolymer-therapeutic agent conjugate in which the biopolymer and therapeutic agent are joined by a disulfide bond. The biologically active conjugate of this invention is useful as a drug delivery vehicle for the in vivo delivery of the therapeutic proteins to specific cells, organs or tissues in a subject. Drug delivery specificity is achieved by appropriate selection of the structure and molecular weight of the biopolymer.

The chemistry used to prepare the conjugates permits the site-specific reaction between the biopolymer and the therapeutic agent. The therapeutic agent contains a reactive thiol group, which can be present in an unmodified version of the therapeutic agent, as in the case of cysteine for example. Alternatively, the thiol group can be introduced into a modified version of a therapeutic agent that does not normally contain a reactive thiol group.

In one embodiment, the therapeutic agent can be reacted, through the reactive thiol group, with a chemically modified version of the biopolymer. This reaction typically occurs at a pH in the range of from about 6.0 to about 10. The biopolymer is activated and modified by reaction with an activating agent, such as a carbodiimide, and reacted with an organic disulfide compound. The organic disulfide compound contains a terminal group, such as an amino group or a hydroxyl group, which is reactive with the carboxylic acid group of the biopolymer in the presence of the activating agent. The reaction of the biopolymer, activating agent and organic disulfide compound occurs at a pH of from about 2.0 to 8.0.

In another embodiment, the therapeutic agent can be reacted, again through the thiol group, with the reducing end of the biopolymer. The biopolymer is first reacted with an organic disulfide compound containing a terminal group, such as an amino group or a hydroxyl group, which is reactive with the terminal carboxyl group of the biopolymer. The reaction of the biopolymer and organic disulfide compound occurs over a wide pH range, typically at a pH of from about 2.0 to 9.0.

In one aspect, the reaction of the biopolymer and therapeutic agent results in the attachment of the biopolymer to the therapeutic agent through a disulfide bond. The linking group or spacer, which can be a lower alkyl, separates the biopolymer from the therapeutic agent. The linking or spacer is a residue resulting from the cleavage of the organic disulfide compound by the reactive thiol of the therapeutic agent.

Typical biopolymers include any of the polyanionic polysaccharides, such as hyaluronic acid and any of its hyaluronate salts, such as sodium hyaluronate, potassium hyaluronate, magnesium hyaluronate and calcium hyaluronate, carboxymethyl cellulose, carboxymethyl amylose, chondroitin-6-sulfate, dermatin sulfate, heparin, and heparin sulfate, as well as polyacrylic acid, polycarbophil, carboxymethyl chitosan, poly-α-glutamic acid, poly-γ-glutamic acid, carrageenan, and sodium alginate. The common feature of the biopolymers of this invention is that they are biocompatible, as that term is defined herein, they contain carboxylic acid functionality, and they can be modified to react with an organic disulfide compound. Such modification can occur, for instance, by reaction of the biopolymer with a suitable activating agent, such as a carbodiimide, to render the carboxylic group vulnerable to nucleophilic attack by, for instance, an amine or a hydroxyl. Alternatively, the modification can occur at the terminal or end group of the biopolymer by reduction of a terminal carbonyl group using a Schiff base.

In a preferred embodiment, the biopolymer is hyaluronic acid having a molecular weight in the range of from about $7.5 \times 10^2$ daltons to about $1 \times 10^7$ daltons. The hyaluronic acid is preferably activated by reaction with an activating agent to render it vulnerable to nucleophilic attack. Suitable activating agents for this purpose include carbodiimides, such as 1-ethyl-3-(3-dimethylaminopropyl) carbodiimide and 1-ethyl-3-(3-dimethylaminopropyl) carbodiimide methiodide.

The organic disulfide compound can be virtually any organic compound having a disulfide bond. Preferably, the disulfide bond is positioned at one end of an alkyl chain, while the other end of the chain terminates in a group reactive with the carbonyl group of the biopolymer. Preferably, the group that reacts with the biopolymer is an amino, carboxyl or hydroxyl group, but most preferably an amino group. In addition to being capable of reacting with the biopolymer, the organic disulfide compound is also capable of reacting with the active thiol group of the therapeutic agent. Preferred organic disulfide compounds include, in general, the nitro-pyridines, thio-pyridines, substituted S-phenyl disulphides, S-sulfonate derivatives, 9-anthrymethyl thioesters, S-carboxymethyl derivatives and nitro-thiobenzoic acid derivatives. More preferably, the organic disulfide compound is a thio-nitro-pyridine, and most preferably 3-nitro-2-pyridinesulfenyl-ethylamine.

The therapeutic agent is preferably one or more of the following: small organic molecules, proteins, nucleic acids, antibodies, peptides, amino acids, lipids, polysaccharides, cell growth factors, and enzymes. More preferably, the therapeutic agent is native or recombinant colony-stimulating factor ("CSF"), an amino acid or glucocerebrosidase. The therapeutic agent should contain a reactive thiol group to react with the modified biopolymer. The reactive thiol group can either be inherently part of the therapeutic agent, as in the case of cysteine, or the reactive thiol group can be introduced into the therapeutic molecule using known techniques. For example, a free thiol group can be introduced into a recombinant therapeutic protein molecule for conjugation and modification. Furthermore, some therapeutic drugs, such as Captopril—a drug used to treat hypertension—inherently contain a free sulfhydryl group as shown in the structure below:

Captopril

The amino groups of therapeutic agents can be conveniently converted into thiols by reaction with Traut's Reagent (aminothiolane).

The therapeutic agent is selected for the particular indication that is to be treated, and the biopolymer is selected, both as to its type and molecular weight, for its ability to target a particular organ, cell or tissue. For instance, a therapeutic agent for treating Gaucher's Disease, a serious liver ailment, is the enzyme glucocerebrosidase. Glucocerebrosidase can be targeted to the liver by forming a conjugate with an appropriately sized hyaluronic acid molecule.

The biologically active conjugate of the present invention provides for improved stability of the therapeutic agent as compared to the use of the unconjugated or unmodified therapeutic agent, or the use of other carriers or conjugated compounds, such as polyethylene glycol ("PEG") or lipids. The improved stability results in increased residence time in the body of a subject and increased circulation time in the blood stream. The conjugates of this invention also display improved targeting to specific tissues, organs and cells. Improved targeting is achieved through the selection of specific types and molecular weights of the biopolymers.

In a further aspect, the invention involves the attachment of a biopolymer onto the surface of a substrate by means of a disulfide linkage. The substrate can be a polymeric material, a ceramic or a metal. Preferably, the substrate is part of a medical device or instrument, such as a stent, graft, suture, catheter, tubing or guidewire. The substrate is modified to contain an amino group, which can then be converted into a thiol group. The substrate can then be reacted with the biopolymer modified with the organic disulfide compound to immobilize the biopolymer onto the substrate.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the preferred methods and materials are now described. All publications mentioned herein, including published patent applications, and issued or granted patents, are hereby incorporated by reference in their entireties. Unless mentioned otherwise, the techniques employed or contemplated herein are standard methodologies well known to one of ordinary skill in the art. The materials, methods and examples are illustrative only and not intended to be limiting.

Other features and advantages of the invention will be apparent from the following description of the preferred embodiments, and from the claims.

DETAILED DESCRIPTION OF THE INVENTION

The biologically active biopolymer-therapeutic agent conjugates of the present invention can be prepared by using a variety of chemical preparatory methods. An important feature of the conjugates of this invention is that the linkage between the therapeutic agent and biopolymer contains a disulfide bond. The disulfide bond is formed by the reaction of the therapeutic agent containing an active thiol with the biopolymer, which has also been modified to contain a disulfide group by reaction with an organic disulfide compound. The procedure for preparing the biopolymer-therapeutic agent conjugates of this invention is described in more detail below.

Prior to the preparation of the conjugate, it is necessary to first select an appropriate biopolymer, and to modify the biopolymer so that it can react with the therapeutic agent and form a disulfide bond. The biopolymer is selected from biocompatible polymers that contain a carbonyl group. The term "biocompatible", as used herein, is intended to denote a substance that has no medically unacceptable toxic or injurious effects on biological function, or which is tolerated by the body. Examples of acceptable biopolymers include the polyanionic polysaccharides, such as hyaluronic acid and any of its hyaluronate salts, such as sodium hyaluronate, potassium hyaluronate, magnesium hyaluronate and calcium hyaluronate, carboxymethyl cellulose ("CMC"), carboxymethyl amylose, carboxymethyl chitosan, chondroitin-6-sulfate, dermatin sulfate, heparin, and heparin sulfate, as well as poly-α-glutamic acid, poly-γ-glutamic acid, carrageenan, and sodium alginate. The term "polyanionic polysaccharide", as used herein, is intended to mean polysaccharides containing more than one negatively charged group, e.g. carboxyl groups at pH values above about a pH of 4.0.

Biopolymers suitable for a particular application are selected from this group of candidate biopolymers on the basis of their ability to target particular tissues, organs or cells, and their in vivo stability, i.e. the in vivo residence time in the circulatory system, or specific tissues, cells or organs. In a preferred embodiment, the biopolymer is hyaluronic acid having a molecular weight in the range of from about $7.5 \times 10^2$ daltons to about $1 \times 10^7$ daltons.

These biopolymers can be "activated" by reacting the biopolymer with a suitable activating agent to render the carboxylic group on the biopolymer vulnerable to nucleophilic attack. Suitable activating agents include carbodiimides, and preferably 1-ethyl-3-(3-dimethylaminopropyl) carbodiimide and 1-ethyl-3-(3-dimethylaminopropyl) carbodiimide methiodide. The reaction between the biopolymer and activating agent occurs in an aqueous medium, preferably at a pH of from about 2.0 to about 8.0, and more preferably a pH of from about 4.0 to about 5.1. Activation of the biopolymer can be useful if the therapeutic agent is linked to the intermediate carboxylic acid groups of the biopolymer.

The activated biopolymer is reacted with an organic disulfide compound. Suitable organic disulfide compounds can be selected from a wide range of molecules, including the nitro-pyridines, thio-pyridines, substituted S-phenyl disulfides, S-sulfonate derivatives, 9-anthrymethyl thioesters, S-carboxymethyl derivatives and nitro-thiobenzoic acid derivatives, and preferably the thio-nitro-pyridines. A particularly preferred organic disulfide compound is 3-nitro-2-pyridinesulfenyl-ethylamine.

In one embodiment, the organic disulfide compound is a compound of general formula

R—L—S—S—M where R is an amino, hydroxyl or carbonyl group, L, if present, is a spacer, preferably a lower normal or iso-substituted alkyl group, and more preferably an ethyl group, each S is a sulfur atom, and M is an organic moiety. The spacer, L, contains a terminal group that is reactive with the activated biopolymer. Preferably, the terminal group is an amino, carboxyl or hydroxyl group, but most preferably an amino group. In addition to being capable of reacting with the biopolymer, the organic disulfide compound is also capable of reacting with the active thiol group of the therapeutic agent.

As shown above, benzyl-3-nitro-2-pyridyl-sulfide is reacted with dichloroethane and sulfuryl chloride to prepare 3-nitro-2-pyridinesulfenyl chloride. The 3-nitro-2-pyridinesulfenyl chloride is reacted with 2-aminoethanethiol and formic acid to prepare 3-nitro-2-pyridinesulfenyl-ethylamine as a precipitated product.

The activated biopolymer can then be reacted with the organic disulfide compound as shown in the following reaction scheme:

G—COOH+R—L—S—S—M→G—COR—L—S—S—M where G is a biopolymer with a pendant carboxyl group, R is preferably an amino group, L, if present, is a spacer, preferably a lower alkyl group, each S is a sulfur atom, and M is an organic moiety. Preferably, the organic disulfide compound is 3-nitro-2-pyridinesulfenyl-ethylamine ("NEA"), and the reaction of NEA and hyaluronic acid, the preferred biopolymer, can be illustrated as shown below, where "EDC" designates 1-ethyl-3-(3-dimethylaminopropyl) carbodiimide, and "HOBt" designates hydroxybenzotriazole:

The preparation of the preferred organic disulfide compound of the present invention, 3-nitro-2-pyridinesulfenyl-ethylamine, can be illustrated as follows:

Alternatively, the biopolymer can be reacted with the organic disulfide compound as shown in the following reaction scheme:

G—CHO+R—L—S—S—M→G—C—R—L—S—S—M where G, R, L S and M are as defined above. Preferably, the organic disulfide compound is 3-nitro-2-pyridinesulfenyl-ethylamine ("NEA"), and the reaction of NEA and hyaluronic acid, the preferred biopolymer, can be illustrated as shown below, where $NaCNBH_3$ is sodium cyanoborohydride:

In the reaction scheme illustrated above, the biopolymer terminal ring opens as a result of a mutarotation equilibrium which occurs naturally in carbohydrates. This forms a terminal aldehyde group, which is the only aldehyde group in the molecule and can form a Schiff base. The aldehyde reacts with the terminal amino group of the organic disulfide compound. The addition of the sodium cyanoborohydride is a well known reaction to reduce the resulting Schiff base. Other reagents which are known to be able to reduce Schiff bases include sodium borohydride, lithium borohydride, lithium cyanoborohydride, sodium aluminum hydride, lithium aluminum hydride, tetrabutyl ammonium cyanoborohydride, sodium amalgam, potassium graphite, and catalytic hydrogenation over platinum or nickel.

As illustrated above, this embodiment results in the attachment of the organic disulfide compound to the reducing end of the biopolymer. This permits the reaction of one mole of organic disulfide compound per mole of biopolymer in a quantitatively controlled manner, which can be result in higher yields, and more precise drug targeting and delivery.

The attachment of the organic disulfide compound need not be restricted to aldehydes inherent in the biopolymer. One could introduce an aldehyde to the biopolymer by a reduction/oxidation sequence as described, for example, by Raja, et al., Analytical Biochemistry 139: 168–177, 171 (1984). Alternatively, one could attach an aldehyde to the biopolymer by modifying an existing functional group of the biopolymer, such as a hydroxyl or carboxyl group. Methods for accomplishing this are well known in the chemical arts. Once the aldehyde is introduced or attached to the biopolymer, the organic disulfide compound may be reacted with the biopolymer as described herein.

The biopolymer-organic disulfide complex is then reacted with a therapeutic agent of choice. The therapeutic agent is selected based on the particular disease state to be treated, and the organ, tissue or cell to be targeted. Suitable therapeutic agents include small organic molecules, proteins, nucleic acids, antibodies, peptides, amino acids, lipids, polysaccharides, cell growth factors, and enzymes. More preferably, the therapeutic agent is native or recombinant colony stimulating factor, an amino acid or glucocerebrosidase.

Glucocerebrosidase is an enzyme which is used to treat a liver condition known as Gaucher's Disease. When glucocerebrosidase is selected as the therapeutic agent, it is advantageous to also select hyaluronic acid, having an appropriate molecular weight, to target the therapeutic agent to liver cells.

The reaction of the therapeutic agent and the HA-NEA complex can be illustrated as shown below:

As shown in the above reaction scheme, the therapeutic agent of choice contains an active thiol (—SH) group, that reacts with the HA-NEA conjugate, displacing the thio-nitro-pyridine residue. The therapeutic agent (shown above as the solid circle) is attached to the hyaluronic acid by a disulfide bond and an amine-terminated ethyl chain (spacer). The reaction occurs at a neutral to basic pH in the range of from about 6–10.

The biologically active conjugates of this invention can be formulated as pharmaceutical compositions for medical diagnosis or treatment, together with appropriate pharmaceutically acceptable carriers and, optionally, other therapeutic or diagnostic agents, using well known formulation protocols. Administration of the pharmaceutical composition can be accomplished using an appropriate vehicle, such as tablets, implants, injectable solutions, and the like. Acceptable carriers include buffering agents and adjuvants. The precise amount of the biologically active conjugate used in the pharmaceutical composition can be determined based on the nature of the condition to be treated, and the potency of the therapeutic agent used. This invention contemplates both local administration and time release modes of administration. As used in this application, the term "subject" is intended to denote a human or non-human mammal, including, but not limited to, a dog, cat, horse, cow, pig, sheep, goat, chicken, primate, rat and mouse.

The process of the present invention can also be employed to modify the surface of a medical device or instrument. A biopolymer, such as hyaluronic acid, can be immobilized onto the surface of a substrate which has been modified to contain, for instance, exposed amino groups, which can be reacted with Traut's reagent and then HA-NEA as shown below:

The aminated surface, prepared, for instance, by cold plasma deposition of an allyl amine, is treated with a reagent, such as Traut's reagent, to convert the amino groups into free thiol groups. The derivatized surface is then reacted with HA-NEA to immobilize HA to the surface by a disulfide bond. The advantage of this approach is the specificity of the reaction for the free sulfhydryl group between the surface and the activated disulfide in the biopolymer. Under these reaction conditions, the activated biopolymer can only react with the surface and not with other biopolymer molecules, thereby creating a modified surface having a well defined biopolymer thickness. By contrast, the use of exogenously added activating agents, such as glutaraldehyde and carbodiimide, to achieve similar results, can result in interpolymer covalent bond formation that can cause uncontrolled increases in biopolymer coating thicknesses. Another advantage is the use of mild reaction conditions, such as the use of an aqueous solvent, ambient temperatures, and a pH in the range of from about 6–10.

This surface modification approach can be used to modify the surface characteristics of stents, to prevent platelet activation and aggregation, or catheter surfaces, to inhibit cell adhesion. An additional advantage of this approach is that the HA will only react with the surface, and not with itself, so the thickness and composition of the HA layer can be readily controlled.

From the above description, one skilled in the art can readily ascertain the essential characteristics of the present invention, and without departing from the spirit and scope of thereof, can make various changes and modifications of the invention to adapt it to various usages and conditions.

As one skilled in the art will appreciate, particular details of the methods of this invention may differ from certain of those methods exemplified herein.

The following examples of the invention are provided by way of illustration only, and are not intended to limit the invention set forth in the appended claims.

EXAMPLE 1

Synthesis of 3-nitro-2-pyridinesulfenyl-ethylamine (NEA)

Benzyl-3-nitro-2-pyridyl sulfide (10 grams, 40.6 mmol.), that had been azeotropically dried by coevaporation with toluene, was dissolved in 1,1-dichloroethane (21 mL). The reaction solution was cooled to 0° C., and sulfuryl chloride (4.24 mL, 52.78 mmol) was added, followed by triethylamine (100 μL, 1.4 mmol). This resulted in a precipitate that was collected, washed with hexane, dried under reduced pressure, and was used without further purification.

The 3-nitro-2-pyridinesulfenyl chloride was added to a solution of 2-aminoethanethiol (4.1 grams, 36.19 mmol) in 230 mL of 90% formic acid. The solution was vigorously stirred for one hour. The resulting precipitate was removed by filtration, and a large volume of diethylether was added to the supernatant. The precipitate was collected, dissolved in warm methanol, and reprecipitated with diethyl ether. 3-Nitro-2-pyridinesulfenyl-ethylamine was obtained in 68% overall yield.

EXAMPLE 2

Synthesis of HA-NEA with 1%–2% NEA Modification

1-Hydroxybenzotriazole ("HOBt") (16.8 mg, 124 μmol) was added to an 8.0% solution (312 μL, 62 μmol) of 70 kdalton HA. To this solution was added NEA (25.0 mg, 93 μmol). The pH of the reaction mixture was adjusted to 3.0 by the addition of 2M HCl. 1-(3-dimethylaminopropyl)-3-ethyl-carbodiimide ("EDC") (35.7 mg, 186 μmol) was added to the acidified reaction mixture, and the mixture was stirred at room temperature for 1.5 hours. All of the above reagents were dissolved in sufficient water to achieve a final HA concentration in the reaction solution of 1%. The reaction was purified by dialysis against phosphate buffered saline ("PBS") for 24 hours, followed by dialysis against water for an additional 24 hours. The product was recovered by lyophilization.

EXAMPLE 3

Synthesis of HA-NEA with 15%–20% NEA Modification

HOBt (16.8 mg (124 μmol) was added to an 8.0% solution (312 μL, 62 μmol) of 70 kdalton HA, followed by the addition of NEA (25.0 mg, 93 μmol). The pH of the reaction mixture was adjusted to 3.0 by the addition of 2M HCl. EDC (71.3 mg, 372 μmol) was added to the acidified reaction mixture, and the mixture was stirred at room temperature for 1.5 hours. All of the above reagents were dissolved in sufficient water to achieve a final HA concentration in the reaction solution of 1%. The reaction was purified by dialysis against phosphate buffered saline ("PBS") for 24 hours, followed by dialysis against water for an additional 24 hours. The product was recovered by lyophilization.

EXAMPLE 4

Synthesis of HA-NEA with 40%–50% NEA Modification

HOBt (16.8 mg, 124 μmol) was added to an 8.0% solution (312 μL, 62 μmol) of 70 kdalton HA, followed by the addition of NEA (25.0 mg, 93 μmol). The pH of the reaction mixture was adjusted to 3.0 by the addition of 2M HCl. EDC (178.3 mg, 930.1 μmol) was added to the acidified reaction mixture, and the mixture was stirred at room temperature for 1.5 hours. All of the above reagents were dissolved in sufficient water to achieve a final HA concentration in the reaction solution of 1%. The reaction was purified by dialysis against phosphate buffered saline ("PBS") for 24 hours, followed by dialysis against water for an additional 24 hours. The product was recovered by lyophilization.

EXAMPLE 5

Synthesis of HA-NEA Using a Mixed Solvent Mixture of 50 Parts N-methylpyrrolidone ("NMP") and 50 Parts Water HOBt (16.8 mg, 124 μmol) was added to an 8.0% solution (312 μL, 62 μmol) of 70 kdalton HA, followed by the addition of NEA (25.0 mg, 93 µmol). The pH of the reaction mixture was adjusted to 3.0 by the addition of 2M HCl. EDC (35.7 mg, 186 µmol) was added to the acidified reaction mixture, and the mixture was stirred at room temperature for 1.5 hours. All of the above reagents were dissolved in a sufficient amount of a 50:50 NMP/water mixture to achieve a final HA concentration in the reaction solution of 1%. The reaction was purified by dialysis against phosphate buffered saline ("PBS") for 24 hours, followed by dialysis against water for an additional 24 hours. The product was recovered by lyophilization.

EXAMPLE 6

Synthesis of HA-NEA Using a Mixed Solvent Mixture of 50 Parts Ethyl Alcohol and 50 Parts Water HOBt (16.8 mg, 124 µmol) was added to an 8.0% solution (312 µL, 62 µmol) of 70 kdalton HA, followed by the addition of NEA (25.0 mg, 93 µmol). The pH of the reaction mixture was adjusted to 3.0 by the addition of 2M HCl. EDC (35.7 mg, 186 µmol) was added to the acidified reaction mixture, and the mixture was stirred at room temperature for 1.5 hours.

All of the above reagents were dissolved in a sufficient amount of a 50:50 EtOH/water mixture to achieve a final HA concentration in the reaction solution of 1%. The reaction was purified by dialysis against phosphate buffered saline ("PBS") for 24 hours, followed by dialysis against water for an additional 24 hours. The product was recovered by lyophilization.

EXAMPLE 7

Synthesis of HA-NEA Using a High Molecular Weight HA

HOBt (33.5 mg, 248 µmol) was added to a 1.0% solution (5 mL, 124 µmol) of 100 kdalton HA, followed by the addition of 50.0 mg (186 µmol) of NEA. The pH of the reaction mixture was adjusted to 3.0 by the addition of 2M HCl. EDC (142.7 mg, 744 µmol) was added to the acidified reaction mixture, and the mixture was stirred at room temperature for 1.5 hours. All of the above reagents were dissolved in sufficient water to achieve a final HA concentration in the reaction solution of 0.2%. The reaction was purified by dialysis against phosphate buffered saline ("PBS") for 12 hours, followed by dialysis against water for an additional 12 hours. The product was recovered by lyophilization.

EXAMPLE 8

HA-NEA Characterization

Figure 1:
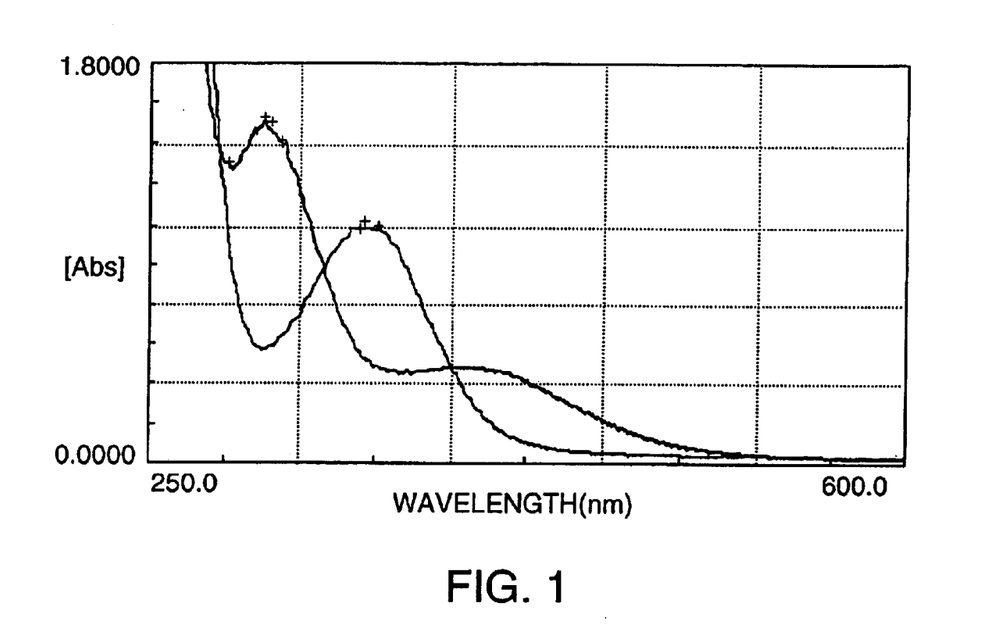
FIG. 1 is a graph illustrating the UV analysis of hyaluronic acid modified with 3-nitro-2-pyridinesulfenyl-ethylamine.
Figure 2:
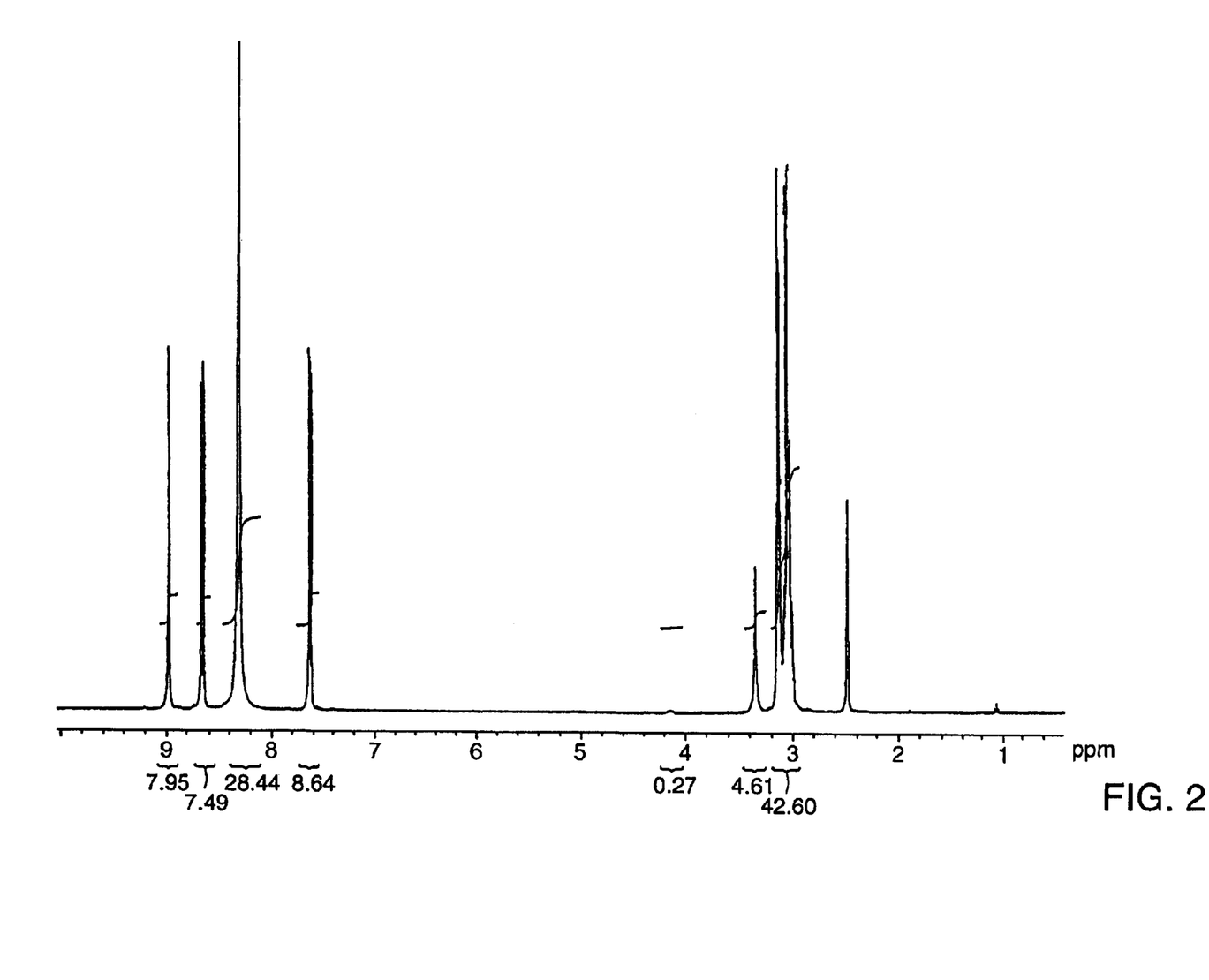
FIG. 2 is an $H^1$ NMR trace of hyaluronic acid modified with 3-nitro-2-pyridinesulfenyl-ethylamine.
Figure 3:
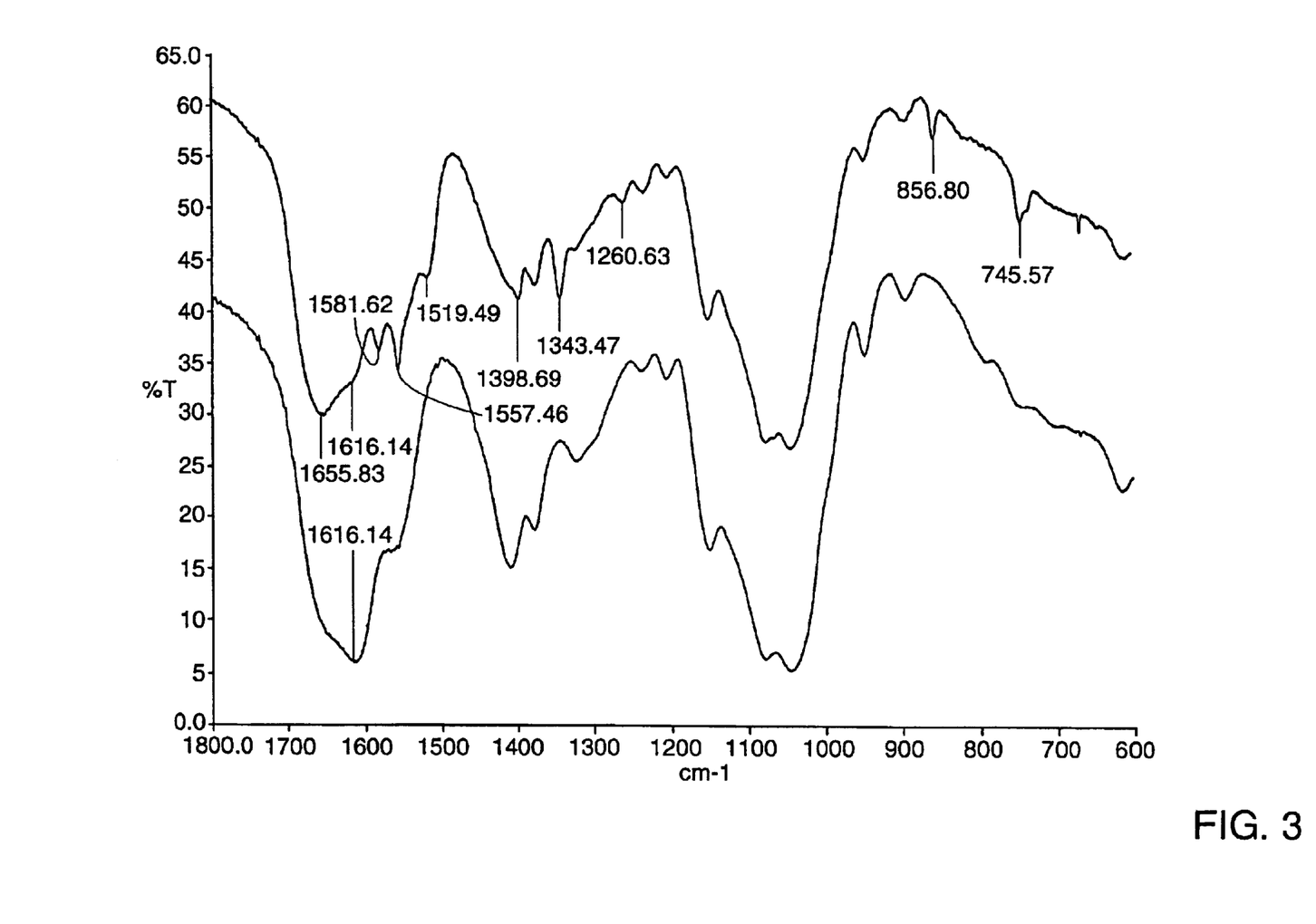
FIG. 3 is a trace of an IR spectra of hyaluronic acid modified with 3-nitro-2-pyridinesulfenyl-ethylamine.

UV analysis of the HA-NEA complex, prepared as described above, reveals a λ max at 345 nm, corresponding to the 3-nitro-2-pyridinesulfenyl group which results in a bathochromic shift to 401 nm upon reduction with DTT (FIG. 1). The $^1$H NMR shows a distinct set of peaks in the aromatic region generated from the 3-nitro-2-pyridinesulfenyl group (FIG. 2). Evidence of the modified HA structure can also be found in the IR spectra (FIG. 3). An amide stretch is observed at 1655 cm$^{-1}$, while the HA carboxyl peak at 1655 cm$^{-1}$ is reduced. The IR spectrum contains additional peaks that can be attributed to the 3-nitro-2-pyridinesulfenyl group, specifically, the aromatic nitro and pyrindinyl stretches occurring at 1557 cm$^{-1}$ and 746 cm$^{-1}$, respectively.

EXAMPLE 9

Synthesis of End-Linked HA-NEA with 35% NEA Modification

NEA (64.5 mg, 240 µmol) was added to 10 mL of a 2.0% solution of HA (60 kdalton, pH 4.1). The reaction was stirred at room temperature for 24 hours, at which time 151 mg (2.4 mmol) of sodium cyanoborohydride was added. The mixture was then stirred for one hour. The mixture was filtered through a 0.45 µm filter and purified by dialysis against 1M NaCl for 24 hours, followed by dialysis against PBS and water for an additional 48 hours. The product was recovered by lyophilization.

EXAMPLE 10

Synthesis of End-Linked HA-NEA with 50% NEA Modification

NEA (64.5 mg, 240 µmol) was added to 10 mL of a 10.0% solution of HA (60 kdalton, pH 4.1). The reaction was stirred at room temperature for 24 hours, at which time 151 mg (2.4 mmol) of sodium cyanoborohydride was added. The mixture was then stirred for one hour. The mixture was filtered through a 0.45 µm filter and purified by dialysis against 1M NaCl for 24 hours, followed by dialysis against PBS and water for an additional 48 hours. The product was recovered by lyophilization.

EXAMPLE 11

Attachment of Cysteine to HA

Dansyl-L-cysteine, in the amount of 2.25 equivalents relative to the amount of 3-nitro-2-pyridinesulfenyl, was added to an HA-NEA (4 mg, 10 µmol) complex. The pH was adjusted to 6.5 with 0.5 M HCl, and the reaction was dialyzed against PBS for 12 hours, followed by dialysis against water for an additional 12 hours. The retentate was then lyophilized to form an HA-cysteine conjugate with the quantitative incorporation of cysteine relative to the amount of 3-nitro-2-pyridinesulfenyl modification.

EXAMPLE 12

Attachment of Cysteine to HA

Dansyl-L-cysteine, in the amount of 2.25 equivalents relative to the amount of 3-nitro-2-pyridinesulfenyl, was added to of an HA-NEA (4 mg, 10 µmol) complex. The pH was adjusted to 8.0 with 0.5 M HCl, and the reaction was stirred at room temperature for 2 hours. The reaction mixture was dialyzed against PBS for 12 hours, followed by dialysis against water for an additional 12 hours. The retentate was then lyophilized to form an HA-cysteine conjugate with the quantitative incorporation of cysteine relative to the amount of 3-nitro-2-pyridinesulfenyl modification.

EXAMPLE 13

Attachment of Cysteine to HA

Dansyl-L-cysteine, in the amount of 2.25 equivalents, relative to the amount of 3-nitro-2-pyridinesulfenyl, was added to an HA-NEA (4 mg, 10 µmol) of complex. The pH was adjusted to 10.0 with 0.5 M HCl, and the reaction was stirred at room temperature for 2 hours. The reaction mixture was dialyzed against PBS for 12 hours, followed by dialysis against D.I. water for an additional 12 hours. The retentate was then lyophilized to form an HA-cysteine conjugate with the quantitative incorporation of cysteine relative to the amount of 3-nitro-2-pyridinesulfenyl modification.

EXAMPLE 14

Attachment of Cysteine to the Reducing-End of HA

Dansyl-L-cysteine, in the amount of 2.25 equivalents, relative to the amount of 3-nitro-2-pyridinesulfenyl, was added to 43 mg (0.64 μmol) of an HA-NEA complex. The reaction was stirred at room temperature for 2 hours. The reaction mixture was dialyzed against 0.1 M NaCl for 12 hours, followed by dialysis against D.I. water for an additional 12 hours. The retentate was then lyophilized to form a HA-Cysteine conjugate.

EXAMPLE 15

Attachment of Ribonuclease A to HA

Dansyl-L-cysteine, in the amount of 2.25 equivalents, relative to the amount of 3-nitro-2-pyridinesulfenyl, was added to an HA-NEA (4 mg, 10 μmol) complex. The pH was adjusted to 10.0 with 0.5 M HCl, and the reaction was stirred at room temperature for 2 hours. The reaction mixture was dialyzed against PBS for 12 hours, followed by dialysis against D.I. water for an additional 12 hours. The retentate was then lyophilized to form an HA-cysteine conjugate with the quantitative incorporation of cysteine relative to the amount of 3-nitro-2-pyridinesulfenyl modification.

Although the foregoing invention has been described in terms of certain preferred embodiments, other modifications, variations and changes can readily be made as will be appreciated by those skilled in the art. It is to be understood that all such modifications, variations and changes are intended to fall within the scope of the present invention as defined by the appended claims.

What is claimed is:

1. A chemically modified biopolymer comprising the following formula:

Wherein G—C(O)— is a biopolymer comprising at least one carbonyl group, —C(O)—, on the biopolymer backbone bound to R, R is an amino group or an oxygen atom, L is a lower alkyl spacer, S is a sulfur atom, and M is an organic moiety; or any pharmaceutically acceptable salt thereof.

2. The chemically modified biopolymer of claim 1, wherein the biopolymer is selected from the group consisting of hyaluronic acid, carboxymethyl cellulose, carboxymethyl amylose, carboxymethyl chitosan, chondroitin-6-sulfate, dermatan sulfate, polycarbophil, heparin, and heparin sulfate.

3. The chemically modified biopolymer of claim 2, wherein the biopolymer is hyaluronic acid.

4. The chemically modified biopolymer of claim 1, wherein the biopolymer is selected from the group consisting of polyacrylic acid, poly-α-glutamic acid, poly-γ-glutamic acid, and alginate.

5. The chemically modified biopolymer of claim 1, wherein the organic moiety is 2-(3-nitro-pyridine).

6. The chemically modified biopolymer of claim 5, wherein the biopolymer is hyaluronic acid and the moiety —R—L—SS—M is (3-nitro-2-pyridinesulfenyl)-ethylamine.

7. The chemically modified biopolymer of claim 1 or 5 wherein R is an amino group.

8. The chemically modified biopolymer of claim 6 wherein the modified biopolymer has a degree of modification in a range of about 1–2%, 15–20%, or 40 to 50%.

9. A chemically modified biopolymer comprising the following formula:

wherein G—C— is a biopolymer having a methylene group, C, bound to R,

R is an imino or amino group;

L is a lower alkyl spacer,

S is a sulfur atom, and

M is an organic moiety; or any pharmaceutically acceptable salt thereof.

10. The chemically modified biopolymer of claim 9, wherein the biopolymer is selected from the group consisting of hyaluronic acid, carboxymethyl cellulose, carboxymethyl amylose, carboxymethyl chitosan, chondroitin-6-sulfate, dermatan sulfate, polycarbophil, heparin, and heparin sulfate.

11. The chemically modified biopolymer of claim 10, wherein the biopolymer is hyaluronic acid.

12. The chemically modified biopolymer of claim 9, wherein the biopolymer is selected from the group consisting of polyacrylic acid, poly-α-glutamic acid, poly-γ-glutamic acid, and alginate.

13. The chemically modified biopolymer of claim 9, wherein the organic moiety is 2-(3-nitro-pyridine).

14. The chemically modified biopolymer of claim 13, wherein the biopolymer is hyaluronic acid and the moiety —R—L—SS—M is (3-nitro-2-pyridinesulfenyl) ethylamine.

15. The chemically modified biopolymer of claims 9 or 13 wherein R is an amino group.

16. The chemically modified biopolymer of claim 14 wherein the modified biopolymer has a degree of modification of about 35% or 50%.

* * * * *